United States Patent
Mandelbaum (10) Patent No.: US 11,759,337 B2
(45) Date of Patent: *Sep. 19, 2023

(54) SYSTEMS AND METHODS FOR FINE MOTOR CONTROL OF THE FINGERS ON A PROSTHETIC HAND TO EMULATE A NATURAL STROKE

(71) Applicant: Scott Mandelbaum, New York, NY (US)

(72) Inventor: Scott Mandelbaum, New York, NY (US)

(73) Assignee: Scott Mandelbaum, New York, NY (US)

(*) Notice: Subject to any disclaimer, the term of this patent is extended or adjusted under 35 U.S.C. 154(b) by 369 days.

This patent is subject to a terminal disclaimer.

(21) Appl. No.: 16/924,696

(22) Filed: Jul. 9, 2020

(65) Prior Publication Data

US 2020/0337869 A1    Oct. 29, 2020

Related U.S. Application Data

(63) Continuation of application No. 15/605,942, filed on May 25, 2017, now Pat. No. 10,758,379.

(Continued)

(51) Int. Cl.
*A61F 2/72* (2006.01)
*A61F 2/58* (2006.01)
(Continued)

(52) U.S. Cl.
CPC ............... *A61F 2/72* (2013.01); *A61B 5/389* (2021.01); *A61B 5/397* (2021.01); *A61F 2/586* (2013.01); *A61F 2002/701* (2013.01)

(58) Field of Classification Search
CPC .... A61F 2/586; A61F 2/68; A61F 2/72; A61F 2002/701; A61B 5/04888
See application file for complete search history.

(56) References Cited

U.S. PATENT DOCUMENTS

| 2,885,686 A | 3/1954 | Giaimo |
| 3,521,303 A | 7/1970 | Yakobson et al. |

(Continued)

FOREIGN PATENT DOCUMENTS

| CN | 103592932 A | 2/2014 |
| CN | 104367405 A | 2/2015 |

(Continued)

OTHER PUBLICATIONS

Bebionic, "Life Changing Myoelectric Hand Packed with the Latest Technology," accessed Apr. 28, 2016, http://bebionic.com/the_hand, 3 pages.

(Continued)

*Primary Examiner* — Christie Bahena
(74) *Attorney, Agent, or Firm* — Cadwalader, Wickersham & Taft LLP (57) ABSTRACT

The present invention generally relates to a system and method for fine motor control of fingers on a prosthetic hand. In particular, the present disclosure describes a system and method for controlling the flexion or extension of one or more fingers of a prosthetic hand to reproduce a natural stroke such as for, e.g., writing, painting, brushing teeth, or eating. The systems and methods described herein use electromyographic (EMG) signals and, more particularly, combinations of electromyographic signals, from muscles in the forearm to activate one or more motors of the prosthetic hand that control the motion of the prosthetic fingers. The electromyographic signals may be used to cause fingers of a prosthetic hand to, for example, imitate a writing stroke while the fingers of the prosthetic hand hold a writing utensil. Additionally, the present invention describes electrode placement locations that maximize peak signal detected while maintaining a low base-line signal.

17 Claims, 10 Drawing Sheets

Related U.S. Application Data (60) Provisional application No. 62/341,395, filed on May 25, 2016.

(51) Int. Cl.
*A61B 5/389* (2021.01)
*A61B 5/397* (2021.01)
*A61F 2/70* (2006.01)

(56) References Cited

U.S. PATENT DOCUMENTS

| | | | |
|---|---|---|---|
| 3,631,542 | A | 1/1972 | Potter |
| 4,452,477 | A | 6/1984 | Hardy |
| 4,623,354 | A | 11/1986 | Childress et al. |
| 5,413,611 | A | 5/1995 | Haslam, II et al. |
| 5,888,213 | A | 5/1999 | Sears |
| 6,344,062 | B1 | 2/2002 | Abboudi et al. |
| 6,379,393 | B1 | 4/2002 | Mavroidis et al. |
| 7,186,270 | B2 | 3/2007 | Elkins |
| 7,655,051 | B2 | 2/2010 | Stark |
| 8,696,763 | B2 | 4/2014 | Gill |
| 8,821,587 | B2 | 9/2014 | Lanier et al. |
| 9,101,499 | B2 | 8/2015 | Haggas |
| 9,114,028 | B2 | 8/2015 | Langenfeld et al. |
| 2012/0150322 | A1 | 6/2012 | Goldfarb et al. |
| 2013/0253705 | A1* | 9/2013 | Goldfarb ............ A61F 2/72 700/260 |
| 2014/0128992 | A1 | 5/2014 | Engeberg |
| 2015/0216679 | A1 | 8/2015 | Lipsey et al. |
| 2015/0351935 | A1 | 12/2015 | Donati et al. |
| 2016/0029947 | A1 | 2/2016 | Girouard |
| 2016/0074181 | A1 | 3/2016 | Segil et al. |
| 2016/0143751 | A1 | 5/2016 | Chestek |
| 2016/0302686 | A1 | 10/2016 | Einarsson |
| 2019/0291277 | A1 | 9/2019 | Oleynik |

FOREIGN PATENT DOCUMENTS

| | | |
|---|---|---|
| CN | 204428215 U | 7/2015 |
| DE | 102007013660 A1 | 9/2008 |
| GB | 2488760 | 9/2012 |
| IN | 0372DEL13 | 2/2013 |
| WO | WO 96/36395 | 11/1996 |
| WO | WO 00/69375 | 11/2000 |
| WO | WO 03/017878 | 3/2003 |
| WO | WO 2015/060793 | 4/2015 |
| WO | WO 2015/114601 | 8/2015 |

OTHER PUBLICATIONS

CBS News, "Bionic DEKA Arm, mind-controlled prosthetic, approved by FDA," dated May 12, 2014, http://www.cbsnews.com/news/bionic-deka-arm-mind-controlled-prosthetic-approved-by-fda/, 4 pages.
CBS, "Creating The Bionic Arm", YouTube Video, dated Apr. 12, 2009, https://www.youtube.com/watch?v=6rloSSqiUCM, 3 pages.
Sarah Adee, "Dean Kamen's 'Luke Arm' Prosthesis Readies for Clinical Trials," dated Feb. 1, 2008, IEEE Spectrum, https://spectrum.ieee.org/biomedical/bionics/dean-kamens-luke-arm-prosthesis-readies-for-clinical-trials, 4 pages.
Kim et al., "Robotic Handwriting: Multi-Contact Manipulation Based on Reactional Internal Contact Hypothesis."(Year: 2014).
Office Actions and Responses from related U.S. Appl. No. 15/605,942, filed May 25, 2017: Corrected Notice of Allowance dated Jul. 9, 2020; Response to Amendment under Rule 312 dated Jun. 23, 2020; Amendment after Notice of Allowance under Rule 312 dated Jun. 18, 2020; Miscellaneous Communication to Application dated Jun. 3, 2020; Notice of Allowance and Examiner Initiated Interview Summary dated Apr. 9, 2020; Amendment and Response to Non-Final Rejection dated Jan. 27, 2020.

* cited by examiner

SYSTEMS AND METHODS FOR FINE MOTOR CONTROL OF THE FINGERS ON A PROSTHETIC HAND TO EMULATE A NATURAL STROKE

CROSS REFERENCE TO RELATED APPLICATION

This is a continuation application of U.S. patent application Ser. No. 15/605,942, filed on May 25, 2017, which claims the benefit of priority under 35 U.S.C. § 119(e) to U.S. Provisional Patent Application No. 62/341,395, filed on May 25, 2016, entitled "Prosthetic Hand," which are hereby incorporated by reference in their entirety.

FIELD OF THE INVENTION

The present invention generally relates to a system and method for fine motor control of fingers on a prosthetic hand. In particular, the present disclosure describes a system and method for controlling the flexion or extension of one or more fingers of a prosthetic hand to reproduce a natural stroke such as for, e.g., writing, painting, brushing teeth, or eating. The systems and methods described herein use electromyographic (EMG) signals and, more particularly, combinations of electromyographic signals, from muscles in the forearm to activate one or more motors of the prosthetic hand that control the motion of the prosthetic fingers. The electromyographic signals may be used to cause fingers of a prosthetic hand to, for example, imitate a writing stroke while the fingers of the prosthetic hand hold a writing utensil. Additionally, the present invention describes electrode placement locations that maximize peak signal detected while maintaining a low base-line signal.

BACKGROUND

Motion of the human body is generally controlled by the contraction of various muscles. Muscular contraction is caused when electrical signals (i.e., "action potentials") travel from the brain, through the central and peripheral nervous systems, and into the target muscle tissue to effect contraction of structural units within the muscle tissue—known as sarcomeres. For example, motion of the fingers of the human hand is controlled by several muscles in the forearm. These forearm muscles contract when electrical signals are sent from the brain, through the central nervous system (i.e., the spine), through the peripheral nervous system (i.e., the arm), and into the muscle tissue to trigger the contraction of the sarcomeres within the muscle tissue. The forearm muscles are connected to the bones of the fingers via tendons such that when the forearm muscles contract, the fingers bend.

To generate an "action potential," a gradient of ions creates a voltage difference across an axon of a neuron. When a threshold voltage difference is exceeded due to the ion gradient, an electrical wave propagates down the length of the axon until it reaches the end of the axon, which may be within muscle tissue. The neuron releases acetylcholine and transfers the action potential to the muscle tissue. The electrical signal will travel through the tissue and trigger the contraction of the individual sarcomeres. One synapse generally controls an entire muscle fiber. One motor neuron usually controls several adjacent muscle fibers. A group of fibers under the control of a single motor neuron is known as a motor unit.

Prosthetic devices have long been used to replace missing body parts, such as hand, arms, and legs. However, these prosthetic devices may be immobile and thus lacking in the same utility that a natural body part imparts. Other prosthetic devices known in the art may use various sensors (e.g., electrodes) to detect the action potential propagation through a muscle—also called electromyography—and use the detection of the action potential as an input signal to control motors that allow the prosthetic device to move. In an example, a prosthetic hand may include one or more motors that control the flexion of individual fingers to mimic the natural flexion of the fingers of a biological hand.

One example of a prosthetic hand known in the art is the Dextrus hand of the Open Hand Project. The Dextrus hand is a prosthetic hand that offers some of the functionality of a human hand by using electric motors instead of muscles and steel cables instead of tendons all packaged within a polymer housing. The electric motors are controlled by electronics (such as a microprocessor) that utilize stick-on electrodes to read signals from the muscles in the forearm, which can control the fingers of the prosthetic hand, causing it to open or close. However, previous implementations of the Dextrus hand were only capable of gripping objects and did not have the capability of fine motor control of the fingers to generate a stroking motion. Thus, a user of previous implementations of the Dextrus hand would have to grip an object and use body parts outside of the prosthetic (e.g., shoulder and/or elbow) to create motion of the object being held. This is inconvenient for the user when performing tasks that would more suitably be performed using fine motor control of the fingers.

Other known prosthetic hands include the i-limb, which is an externally powered prosthesis often controlled by myoelectric signals. However, the i-limb only has preprogrammed grips and does not have the capability of fine motor control of the fingers to generate a stroking motion. A user would have to grip an object with a preprogrammed grip and use joints and/or muscles outside of the finger joints/muscles (such as the shoulder and/or elbow) to create motion of the object being held. Another prosthetic hand, the bebionic3, similarly has preprogrammed grips that are used to hold an object, but does not have the capability of fine motor control of the fingers to generate a stroking motion. Again, a user would have to grip an object with a preprogrammed grip and use joints and/or muscles outside of the finger joints/muscles (such as the shoulder and/or elbow) to create motion of the object being held.

While advances in prosthetic technology have allowed these devices to be manufactured efficiently at low cost, the motion of these prosthetic devices can be difficult to control. Among other issues with control of the prosthetics, no prosthetics have yet addressed the issue of fine motor control of the fingers to generate a stroking motion. Such a motion may be useful for everyday tasks such as writing, painting, eating, brushing teeth, etc. to allow a user to have a more normal life post-amputation of an appendage. Thus, a need exists for systems and methods of controlling prosthetic devices in a way that mimics the fine motor control of the body part the prosthetic intends to replace. With respect to a prosthetic hand, for example, a need exists for systems and methods for fine motor control of the fingers to allow for delicate motion of the fingers, such as forming strokes with a writing utensil.

SUMMARY OF THE INVENTION

In an embodiment, a prosthetic hand includes a hand body, at least two fingers, a controller that utilizes a combination of neuronal signals during a controlled motor activity to determine a threshold. The controller may move at least one finger when the threshold has been exceeded to effect a stroking motion of the at least one finger.

In an implementation, the prosthetic hand further comprises an electrode placed on the surface of the skin, and the combination of neuronal signals may be determined from the electrode. In an implementation, the electrode may be placed on any suitable location on the body where neuronal signals can be detected. The electrode may be placed on a forearm. In an implementation, the combination of neuronal signals may be determined from an implantable device.

In an implementation, the prosthetic hand further comprises a tool held by the at least one finger, and the stroking motion is a stroke of the tool in which surpassing the threshold activates the at least one finger, directly causing the stroking motion. In an implementation, the tool may be a writing utensil. In an implementation, the controller causes the at least one finger to move between a first, inactivated position to a second, activated position. In an implementation, the controller returns the at least one finger to the first, inactivated position after the stroking motion is completed.

In an implementation, the combination of neuronal signals is a ratio of a peak neuronal signal of a muscle during a controlled motor activity to a baseline signal of the muscle without any motor activity. In an implementation, the peak neuronal signal is an average peak signal and the baseline signal is a standard deviation of a previously detected baseline neuronal signal.

In an embodiment, a prosthetic appendage includes an appendage body, at least one digit, and a controller that utilizes a combination of neuronal signals during a controlled motor activity to determine a threshold. The controller may move the at least one digit when the threshold has been exceeded to effect a writing motion of the at least one digit.

In an embodiment, a method of operating a prosthetic hand include determining a baseline neuronal signal of a muscle without any motor activity, determining an elevated neuronal signal of the muscle during a controlled motor activity, computing a threshold based on a combination of the elevated neuronal signal and the baseline neuronal signal such that discrimination between intentional and unintentional muscle contractions can be determined, and facilitating activation of the prosthetic hand when the threshold has been exceeded to effect a writing motion of at least one finger on the prosthetic hand.

In an implementation, the method may include placing electrodes on the surface of the skin and the baseline neuronal signal and the elevated neuronal signal are determined by the electrodes. The electrodes may be placed on the surface of the skin of a forearm. In an implementation, the baseline neuronal signal and the elevated neuronal signal are determined from an implantable device.

In an implementation, the stroking motion generates a stroke of a tool in which surpassing the threshold activates the at least one finger, directly causing the writing motion. In an implementation, the tool is a writing utensil. In an implementation, the activation of the prosthetic hand causes the at least one finger to move between a first, inactivated position to a second, activated position. In an implementation, the method further comprises returning the at least one finger to the first, inactivated position after the stroking motion is completed.

In an implementation, the threshold is further based on a signal-to-noise ratio of the elevated neuronal signal and the baseline neuronal signal. In an implementation, the method further comprises computing summary statistics of the baseline neuronal signal. In an implementation, computing statistics of the baseline neuronal signal consists of computing the standard deviation of the baseline neuronal signal.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout.

DETAILED DESCRIPTION

A prosthetic hand of the invention generally includes a housing, one or more fingers, and one or more motors connected to the fingers via cables. In an embodiment, in place of cables, other means may be used to effect flexion of the finger. In an example, gears may be connected to a motor to effect flexion or extension on a finger. The motors may be controlled by a controller located within or exterior to the prosthetic housing, such as a processor (e.g., an Arduino or other suitable microprocessor) to effect motion of the fingers. The prosthetic hand may further include stick-on electrodes in communication with the controller. In another embodiment, other suitable data input methods as are known in the art may be used to control the prosthetic hand. The electrodes may be placed on the surface of the skin to detect electrical signals from the voluntary contraction of muscles.

In one embodiment, the electrodes are placed on the surface of the skin of the forearm to detect electrical signals from the muscles in the forearm that control the flexion of the fingers. One skilled in the art will recognize that any suitable muscle of the body may be used in place of the forearm muscles to control the prosthetic hand. For example, if no forearm muscles were available, such as when the forearm was amputated, muscles in the upper arm may be utilized to provide an input signal to the electrodes for the controller.

The placement location(s) of the one or more electrodes may correspond to the locations of the muscles that effect flexion of the fingers or other motion of the hand. For example, muscles that may provide useful electrical signals may be any of the following: flexor carpi ulnaris, palmaris longus, flexor carpi radialis, pronator teres, brachioradialis, extensor carpi radialis longus and brevis, extensor digitorum, extensor digit minimi, extensor carpi ulnaris, and aconeus. The electrode may be placed on the skin as a "stick-on" electrode or, alternatively, may be implanted underneath the skin. If the electrodes are implanted, the electrodes may be implanted against the muscle from which it is intended to detect an electrical signal.

To effect motion of the fingers of the prosthetic hand, a baseline signal may be detected by placing one or more electrodes on the surface of the skin of, e.g., the forearm, while the underlying muscles are in a relaxed state (i.e., without any motor activity). The baseline signal may be recorded over a period of time to determine an average baseline signal and to compute summary statistics (e.g., standard deviation, mean, skewdness, or kurtosis) of the baseline signal. Exemplary time periods may be 5 seconds, 10 second, 15 seconds, and 30 seconds. One of skill in the art will recognize that the baseline signal may be recorded for any suitable time period to characterize the baseline signal. Additionally, a baseline difference signal (BDS) may be computed by subtracting the $n^{th}$ baseline signal point from the $(n+1)^{th}$ baseline signal point for k samples. The equation for baseline signal is defined below as Equation 1. Summary statistics (e.g., standard deviation) may be calculated for the baseline difference signal.

$$BDS(n) = (x_{n+1} - x_n)|_{n=1}^{k-1} \qquad \text{(Eqn. 1)}$$

A peak signal may also be detected with a similar setup to that described above for detecting the baseline signal. In this case, the muscles underlying the electrodes may perform a controlled motor activity, such that the muscles are in a contracted state. In an example, one or more fingers of the biological hand may squeeze a spring having a specific, fixed force required to compress the spring (e.g., 1 Newton, 2 Newtons, or 5 Newtons). To detect the peak signal, the one or more fingers may hold the spring compressed for a suitable period of time as described above. A peak signal may be recorded from the contraction of the underlying muscles for the specified period of time. Similar to the baseline signal, an average peak signal and summary statistics (e.g., standard deviation, mean, skewdness, or kurtosis) may be computed using the recorded peak signal. Additionally, a peak difference signal (PDS) may be computed by subtracting the $n^{th}$ peak signal point from the $(n+1)^{th}$ peak signal point for k samples. The equation for peak signal is defined below as Equation 2. Summary statistics (e.g., standard deviation) may be calculated for the peak difference signal.

$$PDS(n) = (x_{n+1} - x_n)|_{n=1}^{k-1} \qquad \text{(Eqn. 2)}$$

A threshold may generally be calculated from any suitable combination of EMG signals. In one embodiment, a threshold may be calculated from the baseline signal and the peak signal to distinguish between an "intended" user motion and an "unintended" user motion. A recorded electromyographic signal that exceeds the threshold indicates an intended user motion while any recorded signal that does not exceed the threshold indicates that no motion is intended. The threshold may be calculated as a ratio of a peak signal value to a baseline signal value. In particular, the ratio may be calculated as an average peak difference signal divided by a standard deviation of the baseline difference signal. The threshold may be a signal-to-noise ratio (SNR). The equation for the threshold is defined below as Equation 3.

$$\text{Threshold} = \frac{PDS_{avg}}{\sigma_{BDS}} \qquad \text{(Eqn. 3)}$$

Once a threshold is determined, the controller may effect motion of the prosthetic hand once this threshold is exceeded. Thus, the method of the present invention effectively acts as a filtering method to filter out electromyographic noise and/or other muscle activity that is not an intended voluntary motion.

Figure 7:
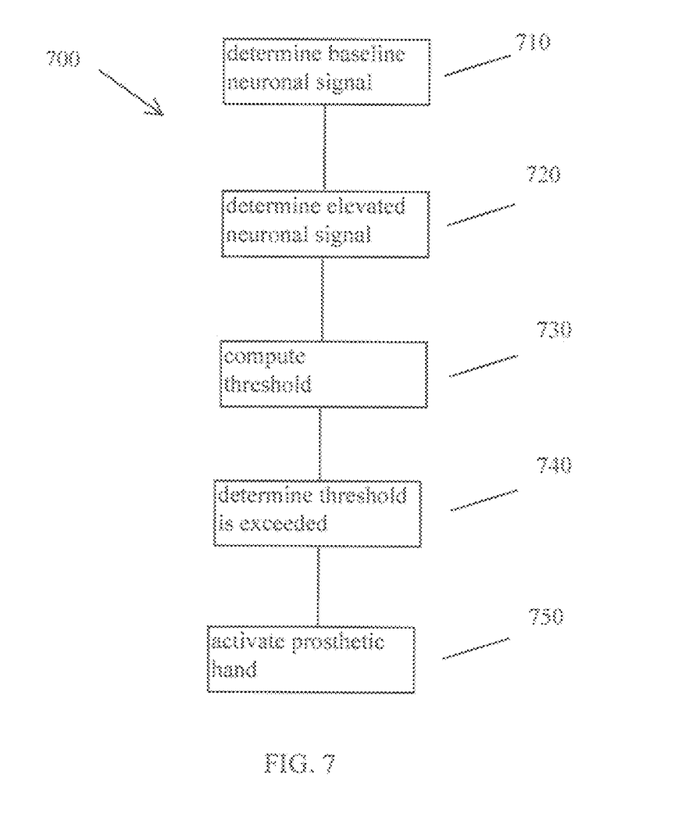
FIG. 7 shows a flow chart of a method according to an embodiment of the invention.

In an embodiment, the controller 130 is configured to perform a method 700 of operating a prosthetic hand, as shown in FIG. 7. The method includes determining 710 a baseline neuronal signal of a muscle without any motor activity, determining 720 an elevated neuronal signal of the muscle during a controlled motor activity, computing 730 a threshold based on a combination of the elevated neuronal signal and the baseline neuronal signal such that discrimination between intentional and unintentional muscle contractions can be determined, determining 740 the threshold has been exceeded, and facilitating 750 activation of the prosthetic hand when the threshold has been exceeded to effect a writing motion of at least one finger on the prosthetic hand.

In an example, the controller may effect motion of one or more fingers to create a stroke of a utensil. The motion and/or activation of the one or more fingers occurs after the utensil is being gripped. The utensil may be, e.g., a writing, drawing, painting, eating utensil, a toothbrush for brushing teeth or any other suitable tool or implement. In particular, the controller may cause the one or more motors housed within the prosthetic to activate (i.e., rotate) at specified speeds to generate a fluid writing stroke motion with the one or more fingers (e.g., three fingers as shown in FIGS. 1D and 1E) contacting the writing utensil. The fluid writing stroke motion of the one or more fingers may create a linear stroke at a distal end of the writing utensil, similar to a writing stroke made by a biological hand when writing. After the one or more motors cause the fingers to move to an activated position (FIG. 1E), the controller then may cause the motors to activate in the opposite direction to cause the fingers to return to their starting position (i.e., inactivated position, shown as FIG. 1D). Thus, the prosthetic hand of the present invention may be used to allow users to write in a similar fashion as with a biological hand by generating a fluid writing stroke motion with one or more fingers of a prosthetic hand.

One skilled in the art will recognize that these techniques for controlling the motion of a prosthetic hand can be used in any suitable prosthetic, such as, for example, a prosthetic foot, leg, or arm. Moreover, the techniques, methods, and systems described herein can be applied in other suitable applications, such as exoskeletons, or industrial applications, such as for industrial robots. In each case, one skilled in the art will recognize that a different muscle or set of muscles may be used to provide the input signal to the prosthetic controller and to effect motion of the prosthetic or other device.

Figure 1A:
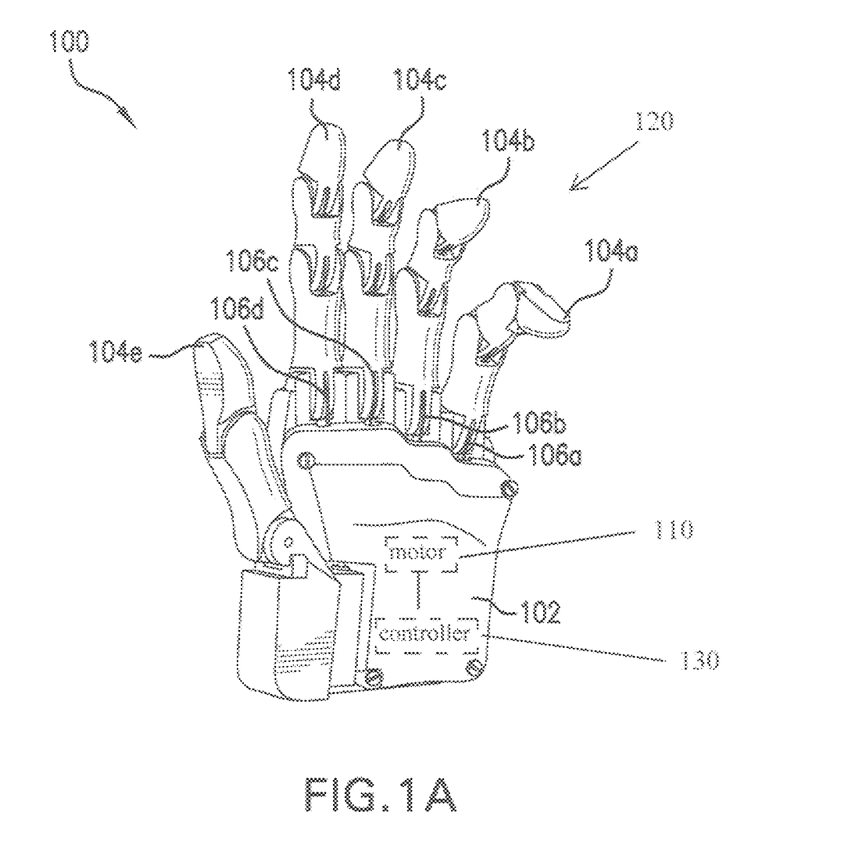
FIG. 1A shows an isometric view of an exemplary prosthetic hand.
Figure 1B:
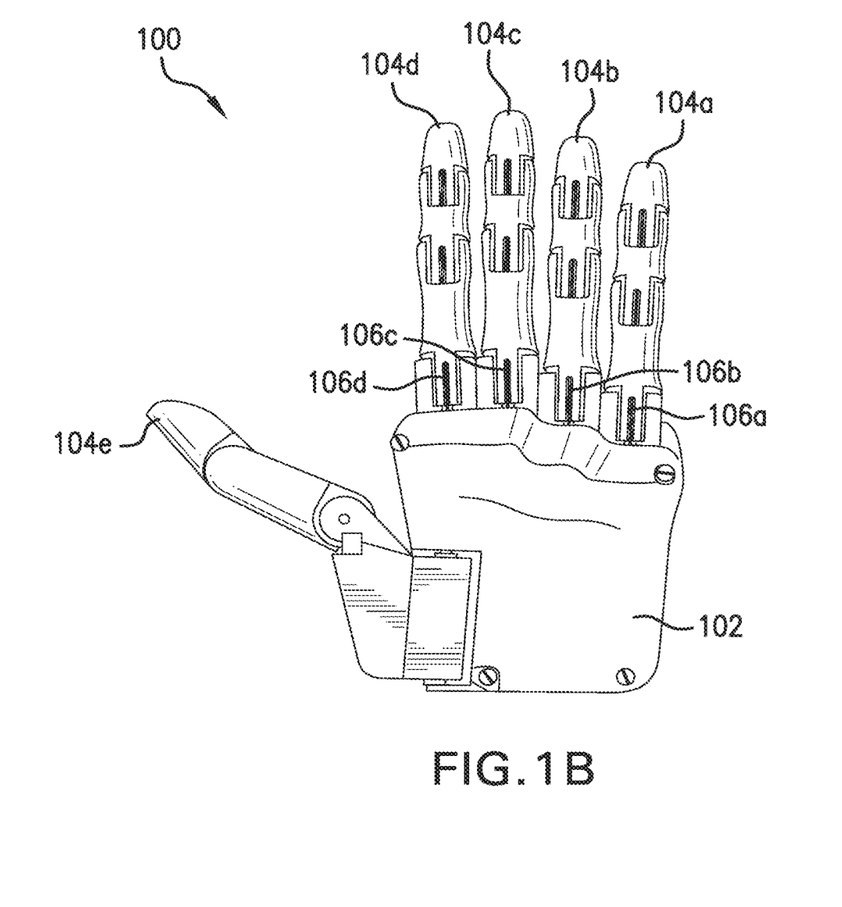
FIG. 1B shows a top view of an exemplary prosthetic hand.
Figure 1C:
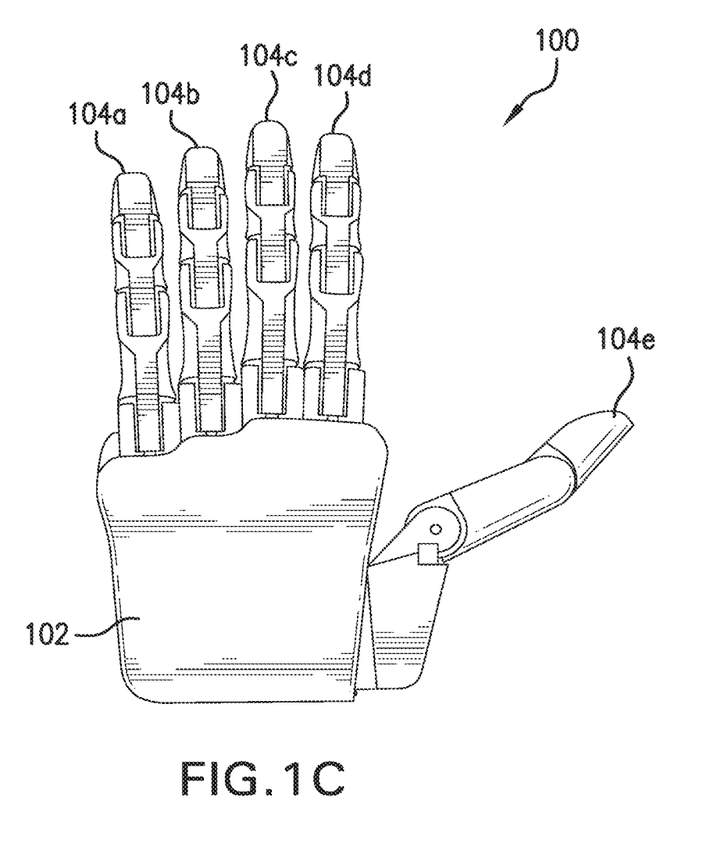
FIG. 1C shows a bottom view of an exemplary prosthetic hand.
Figure 1D:
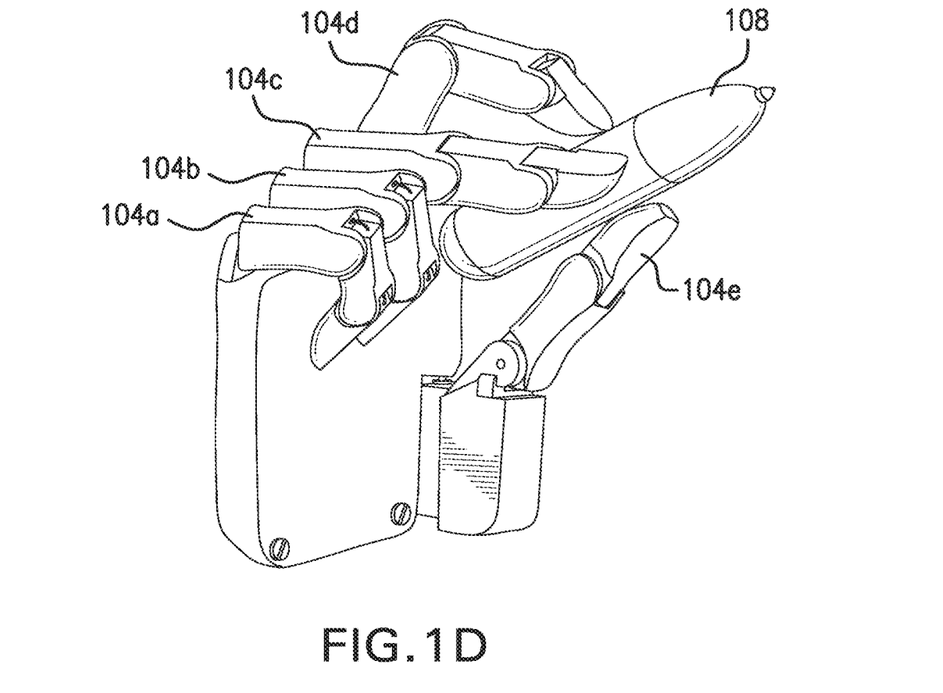
FIG. 1D shows an isometric view of an exemplary prosthetic hand holding a pencil in a non-activated state.
Figure 1E:
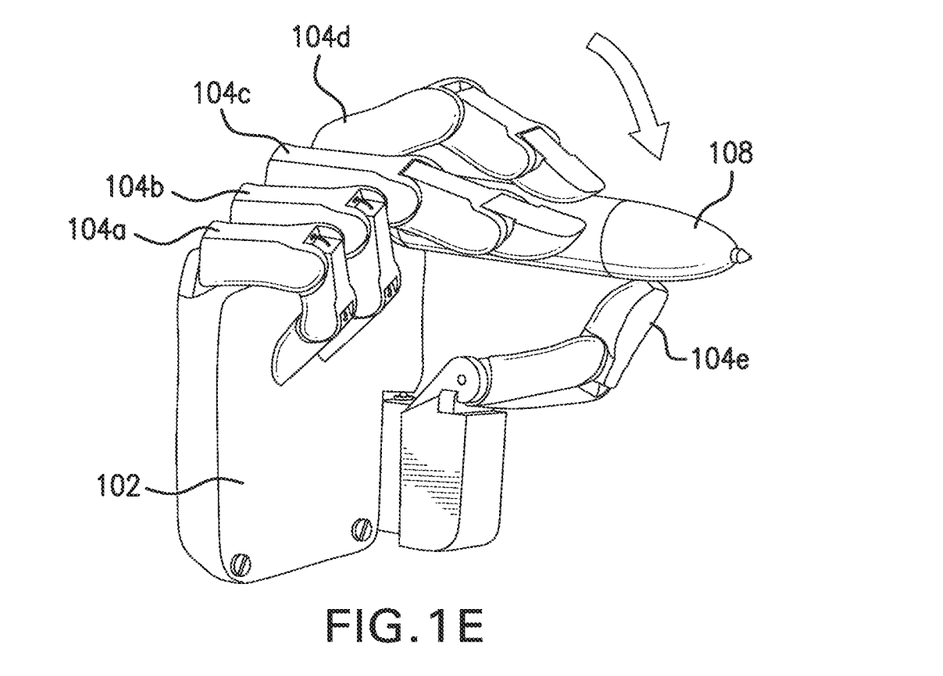
FIG. 1E shows an isometric view of an exemplary prosthetic hand holding a pencil in an activated state during a writing stroke motion.

FIGS. 1A-1C show an exemplary prosthetic hand 100 of the present invention. Prosthetic hand 100 includes a housing 102 having fingers 104a-104e. Each of fingers 104a-104 includes at least two joints that allow the respective finger to move just like a biological hand. The prosthetic hand 100 further includes cables 106a-106d that act as "artificial tendons" and each cable is connected to a motor 110 (shown in FIG. 1A) disposed within the housing 102. The motor 110 may be controlled by a controller 130 located within or exterior to the prosthetic housing 102 to effect motion of the prosthetic hand 100. The cables may be made of a metal, such as steel, titanium, or any suitable metal alloy as is known in the art. Alternatively, the cables 106a-106d can be made of a polymer. Furthermore, the housing is preferably made of a polymer, such as polyethylene, polypropylene, polyethylene terephthalate, ABS, or any other suitable polymer or combination of polymers as is known in the art.

FIGS. 1D and 1E shows an isometric view of an exemplary prosthetic hand 100 holding a pencil. In FIG. 1D, the prosthetic hand 100 is gripping a writing utensil (e.g., a pencil or pen) 108 with three (3) fingers 104c-104e in a non-activated state, which corresponds to the middle finger 104c, index finger 104d, and thumb 104e. One of skill in the art will recognize that any suitable number of fingers may be used to grip the pencil. During detection of electric signals from the muscles, upon exceeding the threshold (as described in more detail above), the controller causes the three fingers 104c-104e gripping the writing utensil 108 to generate a stroke of the writing utensil 108. The stroke may be a linear stroke of a writing utensil or any other suitable stroke that a user would naturally perform while writing or painting, for example. FIG. 1E shows an activated state of the prosthetic hand after the fingers have performed a writing stroke motion. The writing stroke motion may be repeated over and over again to simulate natural writing by causing the muscles near the electrodes to contract and generate a signal that exceeds the specified threshold.

In the non-activated state shown in FIG. 1D, the writing utensil 108 is angled slightly above a horizontal and the thumb 104e is supporting the bottom of the writing utensil 108. The thumb 104e is not bent at the joints and is substantially straight. The middle finger 104c is also substantially straight (i.e., the middle finger is not bent at any of the joints) and supports a side of the writing utensil 108. The index finger 104d is curled such that a proximal joint of the index finger 104d in FIG. 1D is higher than the same proximal joint in FIG. 1E. The index finger 104d also includes a bend at a distal joint (between a distal segment and a middle segment of the index finger 104d) such that a distal segment of the index finger 104d slopes downwardly more than the middle segment of the index finger 104d.

In the activated state shown in FIG. 1E, the writing utensil 108 is at an angle slightly below the horizontal. The thumb 104e is angled such that the proximal segment of the thumb 104e is substantially horizontal and the joint of the thumb 104e is now angled such that the distal segment of the thumb 104e is substantially the same slope as the entire thumb 104e in the non-activated state of FIG. 1D. The fingertip and some of the finger pad of the thumb 104e now support the writing utensil 108. The proximal segment of the index finger 104d is now angled further downwardly. The angle created at the distal joint of the index finger 104d is larger, since the finger is almost completely straight. The middle segment of the index finger 104d angled downwardly. However, the distal joint of the index finger 104d has substantially no bend, as the middle segment and the distal segment now are substantially straight. A proximal segment and a middle segment of the middle finger 104c both remain substantially horizontal with one another (i.e., there is no bend at the distal joint of the middle finger 104c). However, a distal joint of the middle finger 104c has a downward bend, such that the combined middle segment and distal segment of the middle finger 104c are now angled slightly downwardly to follow the motion of the writing utensil 108.

Figures 2A, 2B, 2C:
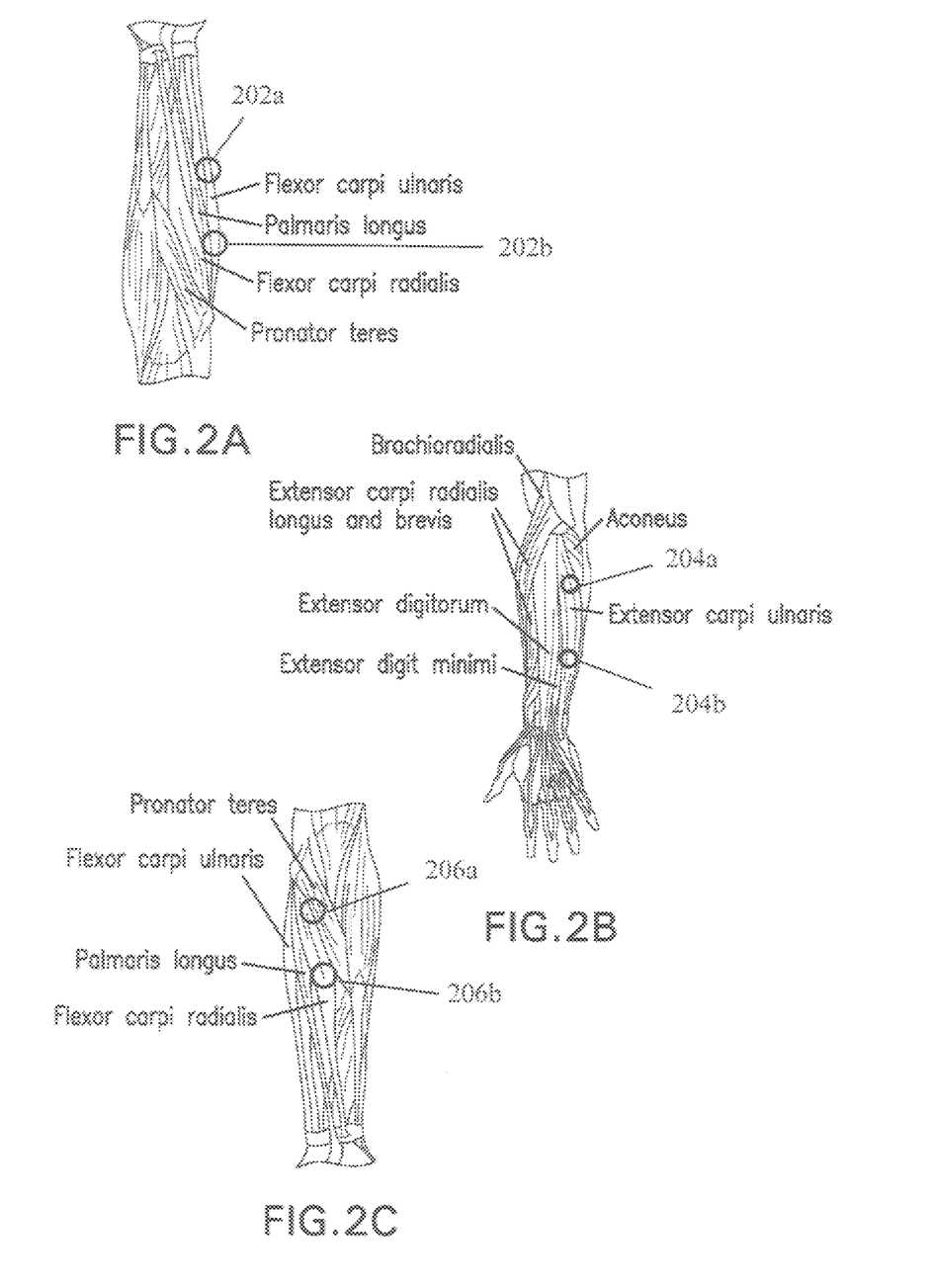
FIG. 2A shows an illustration of musculature and flexor carpi ulnaris electrode placement.
FIG. 2B shows an illustration of musculature and brachioradialis electrode placement.
FIG. 2C shows an illustration of musculature and flexor carpi radialis electrode placement.

FIGS. 2A-2C show an illustration of musculature electrode placement. In particular, FIG. 2A shows the placement of electrodes 202a, 202b, which are positioned to detect electrical signals from the flexor carpi ulnaris. FIG. 2B shows the placement of electrodes 204a, 204b, which are positioned to detect electrical signals from the brachioradialis. In another embodiment, the electrodes 204a, 204b may be positioned to additionally detect electrical signals from the extensor carpi radialis. FIG. 2C shows the placement of electrodes 206a, 206b, which are positioned to detect electrical signals from the flexor carpi radialis. In another embodiment, the electrodes 206a, 206b may be positioned to additionally detect electrical signals from the pronator teres.

Figure 3A:
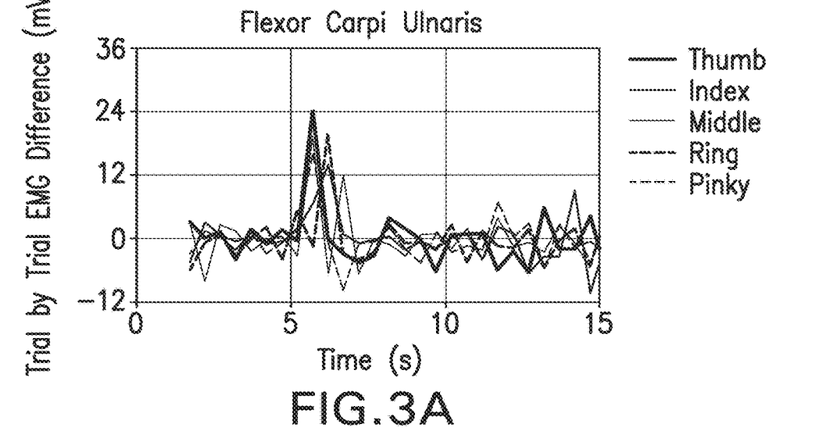
FIG. 3A shows a graph representing the electromyography of the flexor carpi ulnaris.
Figure 3B:
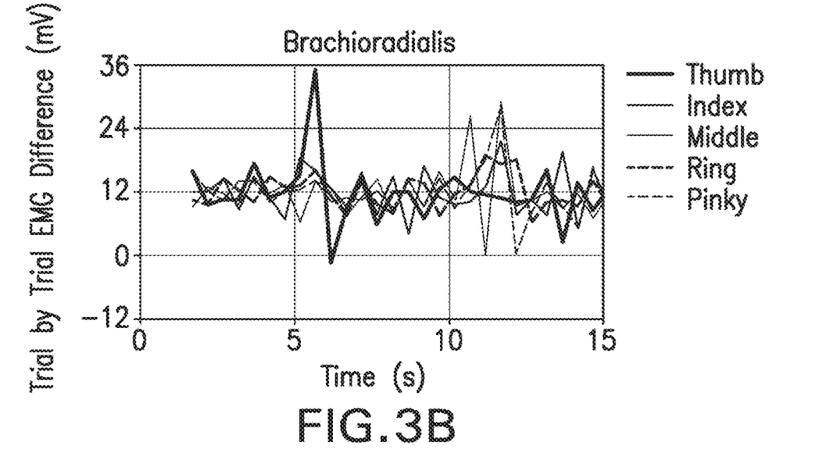
FIG. 3B shows a graph representing the electromyography of the brachioradialis.
Figure 3C:
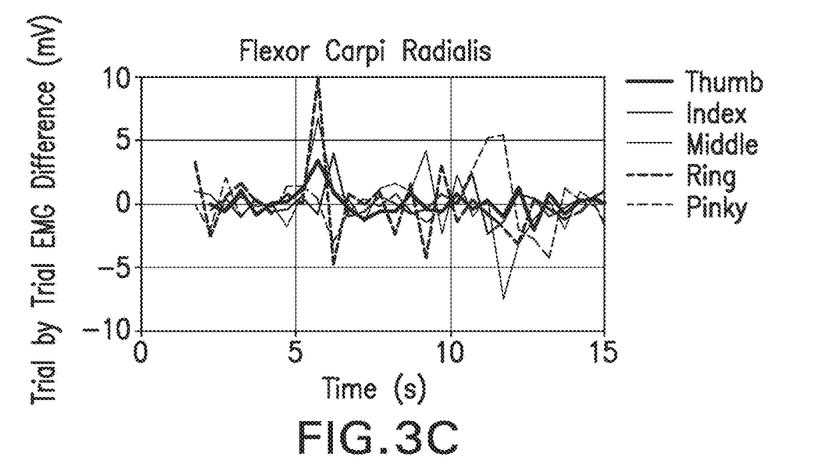
FIG. 3C shows a graph representing the electromyography of the flexor carpi radialis.

FIG. 3A shows a graph representing the electromyography of the flexor carpi ulnaris. FIG. 3B shows a graph representing the electromyography of the brachioradialis. FIG. 3C shows a graph representing the electromyography of the flexor carpi radialis.

Figure 4A:
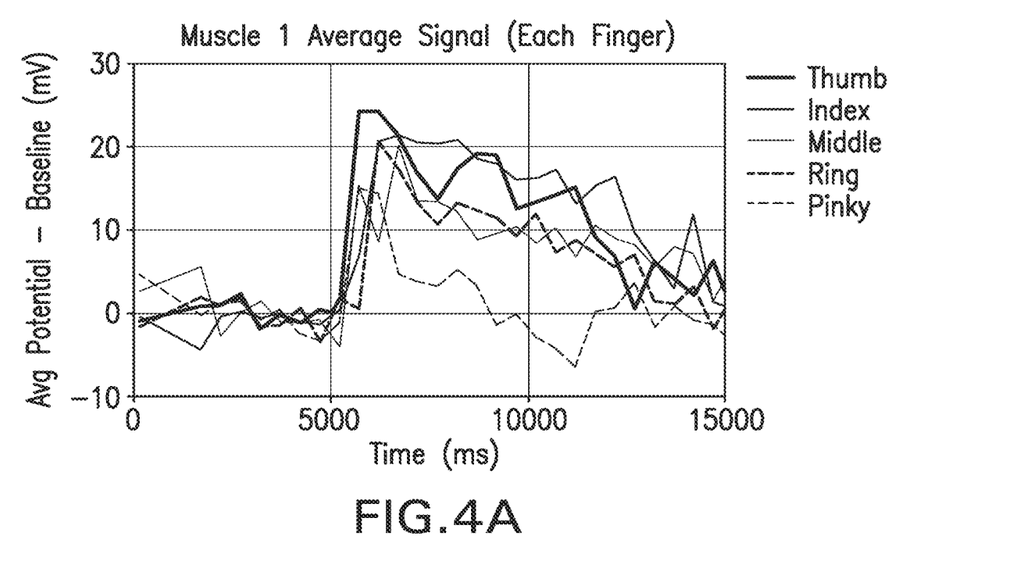
FIG. 4A shows a graph of average flexor carpi ulnaris EMG signal for each finger.
Figure 4B:
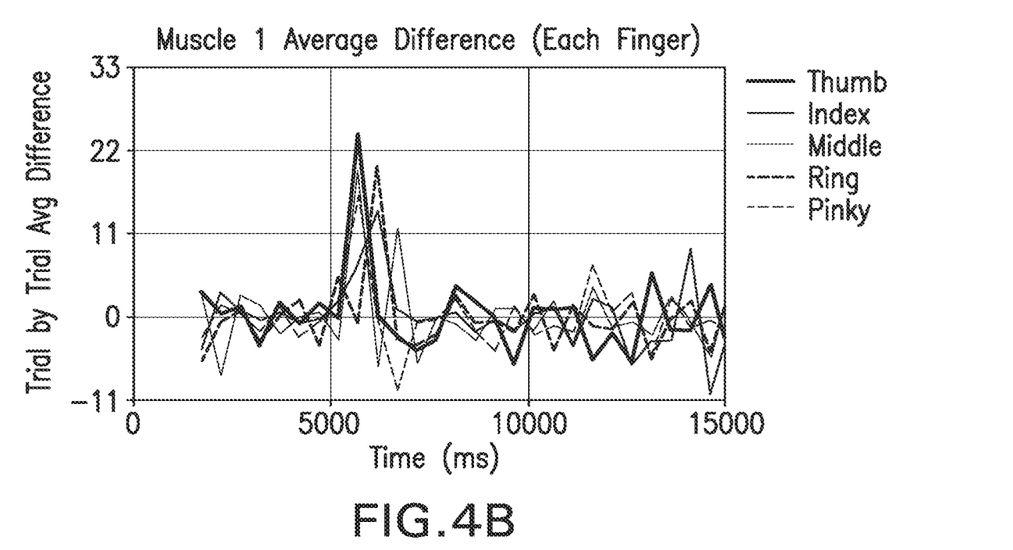
FIG. 4B shows a graph of average trial-by-trial difference in flexor carpi ulnaris EMG signal for each finger.

FIG. 4A shows a graph of average flexor carpi ulnaris EMG signal for each finger. FIG. 4B shows a graph of average trial-by-trial difference in flexor carpi ulnaris EMG signal for each finger. As can be seen in FIGS. 4A and 4B, a peak appears shortly after 5000 ms representing the time at which the subject voluntarily activated the specific finger to compress a spring scale. The data from FIGS. 4A and 4B suggest that the flexor carpi ulnaris may be a candidate for electromyographic threshold detection for activating a prosthetic to generate motion.

Figure 5A:
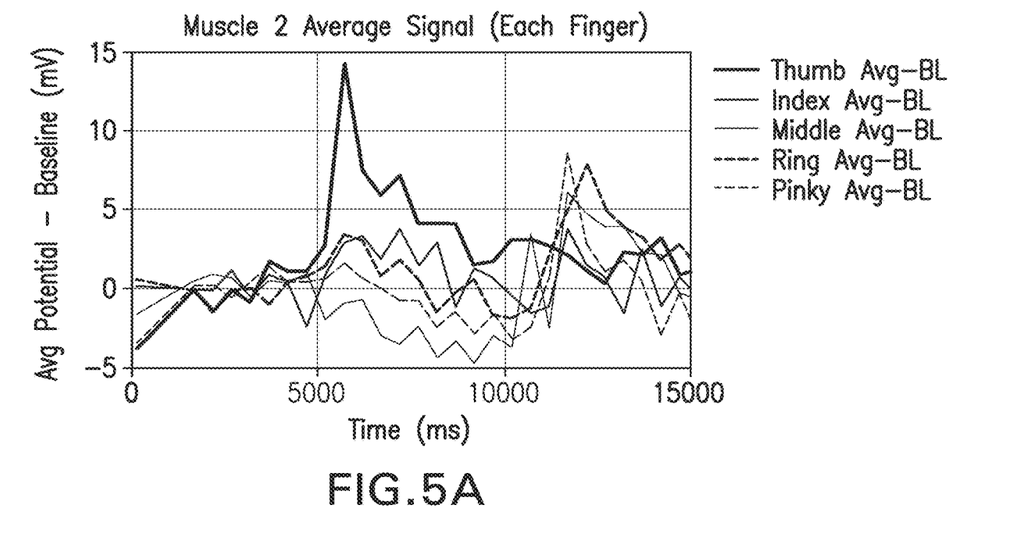
FIG. 5A shows a graph of average brachioradialis EMG signal for each finger.
Figure 5B:
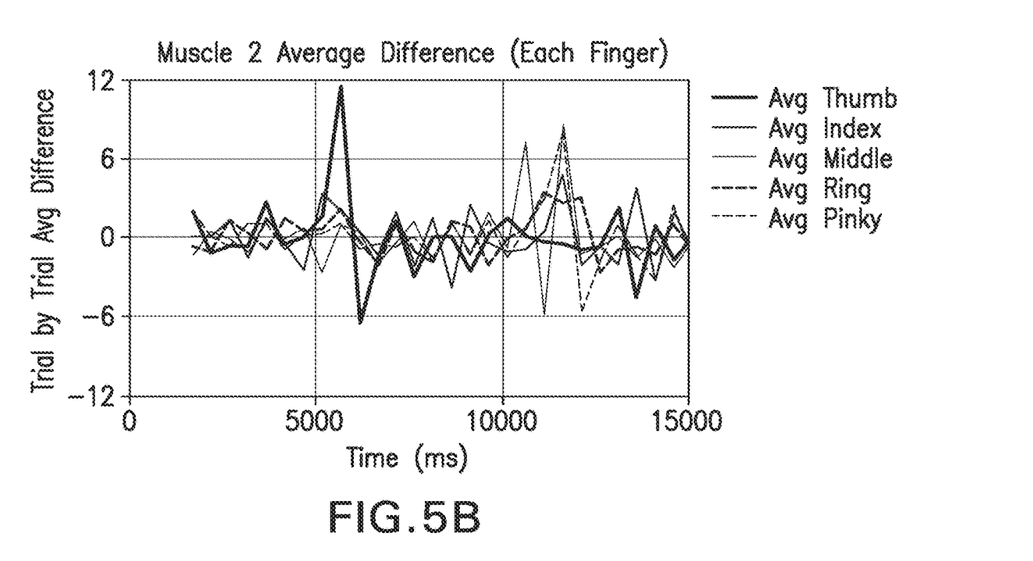
FIG. 5B shows a graph of average trial-by-trial difference in brachioradialis EMG signal for each finger.

FIG. 5A shows a graph of average brachioradialis EMG signal for each finger. FIG. 5B shows a graph of average trial-by-trial difference in brachioradialis EMG signal for each finger. FIGS. 5A and 5B shows a noisy signal for each finger and no discernible peaks for more than one particular finger.

Figure 6A:
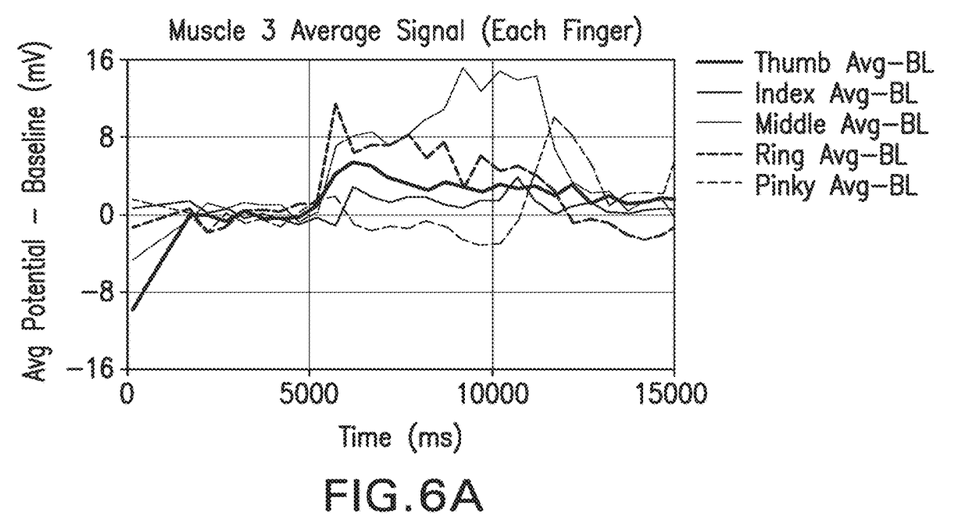
FIG. 6A shows a graph of average flexor carpi radialis EMG signal for each finger.
Figure 6B:
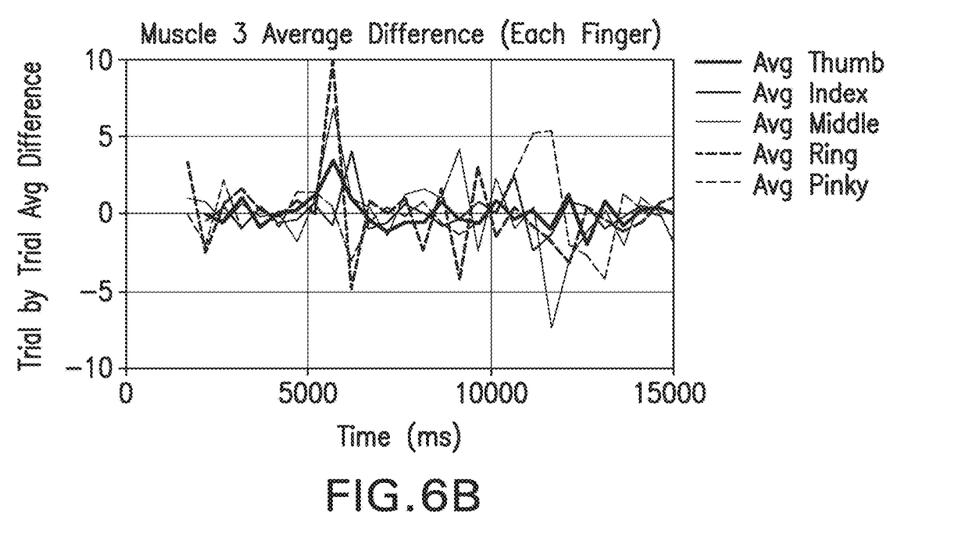
FIG. 6B shows a graph of average trial-by-trial difference in flexor carpi radialis EMG signal for each finger.

FIG. 6A shows a graph of average flexor carpi radialis EMG signal for each finger. FIG. 6B shows a graph of average trial-by-trial difference in flexor carpi radialis EMG signal for each finger. FIGS. 6A and 6B shows discernible peaks for some fingers but is generally considered a noisy signal. The data from FIGS. 6A and 6B suggest that the flexor carpi radialis and/or the pronator teres may be a candidate for electromyographic threshold detection for activating a prosthetic to generate motion.

Experimental tests were performed to characterize EMG signals from various muscles and compute an appropriate threshold that indicates whether a user intends to generate a writing stroke motion. The experimental setup and results are discussed in more detail below.

The aim of this research was to quantify and characterize the electromyographic potential of several forearm muscles during a controlled motor activity. As this information will be used to develop a control algorithm for a neuroprosthetic hand (prototype shown above as FIGS. 1A-1E), a further goal was to find electrode placements that provide a consistently low baseline signal and consistently high peak signal, allowing for clear discrimination between intentional and unintentional muscle contractions. Ultimately, upon exceeding a predetermined threshold, the activation of prosthetic movement will be initiated.

Methods: Surface EMG recordings were made from three muscles, the flexor carpi ulnaris, flexor carpi radialis and brachioradialis, of the right forearm of a single subject. For each trial of a specific motor task, the subject remained still (i.e., having no motor activity in the target muscles) for 5 seconds to obtain a baseline EMG reading. The subject then flexed a finger over a 1 second period to apply a force of 2 Newtons against a spring scale. This force was sustained for 5 seconds, after which the subject relaxed the finger over a 1 second period, returning to the original, relaxed position for an additional 5 seconds. This procedure was repeated five times for each digit on right hand, giving a total of 25 trials per muscle. The average and standard deviation of the EMG signal for each digit/muscle combination was then calculated. The difference of the EMG signal value at each timepoint and the preceding time point was also determined. Finally, the signal-to-noise ratio (SNR) was calculated for each digit/muscle combination by taking the average peak difference value and dividing it by the standard deviation of the corresponding baseline difference value.

Results: Of the 75 trials (25 per muscle×3 muscles), all successfully yielded EMG recordings. For the flexor carpi ulnaris, peaks corresponding to the onset of motor activity were evident for all five digits (FIG. 3A). Such peaks were largely absent for the brachioradialis muscle (FIG. 3B) and were of lower magnitude for the flexor carpi radialis muscle (FIG. 3C). Motor activation by the thumb yielded the highest SNR value (4.6) for the flexor carpi radialis; the lowest SNR value (2.3) was associated with the little finger.

Conclusions: Results indicated that the flexor carpi ulnaris muscle consistently yielded the clearest EMG signal associated with deliberate onset of muscle activity, and is an excellent candidate for use in neuroprosthetics.

This research is a stepping-stone toward successfully implementing a low-cost prosthetic hand optimized for efficient handwriting through finger movement. Natural manual handwriting requires a complex set of finger motions that have not been adequately addressed in prostheses at this time in prosthetics currently on the market. However, the relatively recent development of consumer grade 3D printer technology has the potential to revolutionize the prosthetics world, opening up both development of and access to these critical medical devices. While current low-end prosthetic hands may generally feature the ability to grip a pencil firmly for writing, movement of the gripped object (e.g., a pencil) needs to be done outside of the prosthetic (e.g., with a shoulder and/or elbow). All of the necessary movements for writing are generated from body parts outside the hand itself in current models of prosthetics. Amputees instead rely on their elbows and shoulders to produce the fine strokes required to draw lines and curves, significantly limiting their legibility, speed, and endurance. This is inconvenient for a user and does not lend to a high fidelity prosthetic as these low-end prosthetics cannot generate stroking motions used in everyday life such as those motions used in writing or painting.

The long-term goal of this project is thus to provide amputees with another degree of freedom when writing, specifically fine motor control of the fingers. Such a development would allow for more efficient and accurate movements, enabling faster and more natural writing. Moreover, improved prosthetic dexterity would help reduce the strain on arm and shoulder muscles associated with using them for unnaturally fine motor tasks, improving the comfort of the user.

Although highly dexterous designs have been developed in recent years, myoelectric prosthetics capable of intricate movements and that respond to users' muscle activity as inputs are often prohibitively expensive, in the range of $20,000 to $100,000. Even with these highly dexterous designs, none have the capability of forming a natural stroke such as the motion used when writing or painting. While the majority of people cannot afford these advanced prosthetics, the advent of 3D printing and versatile small electronics has the potential to bring a similar degree of technological sophistication to the masses. This technology has the potential to reduce the cost on such a device to orders of magnitude below what is currently on the market. For instance, the plastic necessary to print a prosthetic hand only costs around $5-10.

Similarly, small electronic devices designed to record electrical activity in human muscles (i.e., electromyographs) can be obtained for under $100, and can enable the kinds of direct muscular control currently only available in the most expensive prosthetics. Additional materials such as motors and signal processing equipment are also now extremely affordable, with the total estimated cost for a 3D printed myoelectric prosthetic hand in the neighborhood of $200-$250.

In addition to the cost benefits, customized, high-end 3D printed prosthetics have the potential to alleviate much human suffering and improve quality of life. For amputees, a major determinant of quality of life is independence and the ability to perform everyday activities normally or with minimal adaptation. One such domain is writing, which most people perform daily and, for those with biological fingers, entails a series of highly complex motions. Consequently, amputees may feel substantially more "normal" if they are able to produce fluent writing with naturalistic finger movements. Bringing such advances to those of low socioeconomic status is particularly critical, as they are often the most adversely affected by the social and economic hardships of disfigurement and amputations. Thus, a prosthetic hand of the present invention may be affordable to low-income individuals and/or impoverished nations to allow those with a hand amputation or other debilitating condition of the hand to communicate through writing.

In line with these goals, this experiment represents the first steps toward achieving a low-cost myoelectric prosthetic hand specialized for writing by characterizing the electric activity of several muscles that will ultimately control the movement of prosthetic fingers. It was hypothesized that 1) the EMG recording setup would be able to distinguish intentional motor activity from the background level of activity for each muscle tested, but 2) the muscles would vary in how clearly this intentional motor activity could be identified.

The general experiment was as follows: 1) electrodes were placed on forearm muscle groups of interest during a spring pulling task; 2) at regular intervals, the EMG recorded the amplitude of electric potential caused by neuromuscular activity through these electrodes; 3) using custom code (optionally, in combination with open source code), the processing unit received analog signals from the EMG and translated them into digital potential readings; 4) these readings were recorded and saved to file for later analysis; and 5) these recordings were analyzed and characterized. The findings from this experiment informed the development of algorithms for controlling prosthetic fingers to emulate manual handwriting by directly interfacing with forearm musculature.

EMG Setup: Electrodes for the EMG were placed on three muscles, as depicted in FIGS. 2A-2C. While the recordings were clearly made from the superficial muscles of the forearm, it was difficult to determine precisely which of these muscles were targeted for each recording. The three most likely candidates were selected based on anatomical landmarks on the surface of the arm and anatomical reference data. These were the flexor carpi ulnaris (FIG. 2A); the brachioradialis (FIG. 2B); and the flexor carpi radialis (FIG. 2C). For each site, the positive electrode was placed on the center of the muscle, the negative electrode was placed at the distal edge of the muscle, and a ground electrode was placed on the bony protuberance of the elbow. Once placed, the electrodes were connected to the EMG module, which was in turn connected to the Arduino control module and tested before proceeding.

Writing Force Estimation: In a separate experiment, two test subjects each applied pressure with pencil in hand to a piece of paper on top of a triple beam balance. The subjects then simulated writing on the paper; the mass needed to balance out this writing force was used to calculate the approximate force used when writing. This yielded a mass reading of 200±5 grams for both test subjects, corresponding to a force of approximately 2N; this value was subsequently used in the Motor Task (see below).

Recording Setup: Upon proper setup and documentation regarding to the location of the electrodes, a spring scale was hung from a wooden stabilizer attached to a table. For each recording site, each of the fingers (i.e., thumb, index, middle, ring, and little finger) was latched onto the spring scale one at a time. Recordings were initialized by uploading code (modified from code provided by the EMG manufacturers) to the control module; simultaneously, a stopwatch was started. The uploaded code allowed the electric potential changes detected by the EMG to be quantitatively measured and recorded; the output from this setup was in the form of electric potential (mV) and time since start of recording (ms). These times were crosschecked against the time displayed on the stopwatch to verify accuracy.

Motor Task: For each trial, the test subject was instructed to remain as still as possible for five seconds to obtain a steady baseline EMG reading. After five seconds, the test subject was instructed to bend the finger over a 1 second period to reach a reading of 2 Newton on the spring scale. The subject was instructed to maintain this 2 Newton force in this position for 5 seconds. The process was then reversed, with the subject relaxing the finger over a 1 second period until the spring scale read 0 Newtons. The subject remained in this position for an additional 5 second, after which the recording was terminated and saved to file. For each EMG site, this procedure was repeated five times per finger, giving a total of twenty-five trials per recording site; three sites were tested in this manner (flexor carpi ulnaris, brachioradialis, and flexor carpi radialis; see above).

Data Analysis: The EMG data for each trial arrived in the form of an electric potential readout with an initial sample around 130 ms after recording was initialized, then additional samples at regular intervals set to once every 500 ms starting at 1,700 ms. To quantify the sensitivity of the EMG to changes in neuromuscular activity, the difference between each reading and the preceding reading was also calculated. The "peak" change in neuromuscular activity was therefore defined as the largest reading-by-reading difference value within a 2,000 ms window centered around 5,200 ms, to account for variation in the timing of the subject. This corresponded to the closest measurement time to the target muscle activity onset time of 5 seconds. For each finger and each muscle site, the reading times were then shifted such that the difference peaks were aligned, as these varied somewhat between trials. The "baseline" epoch was then defined as the readings that preceded the determined peak time point for each trial. Thus, four summary statistics were generated: average baseline EMG reading, average peak EMG reading, average baseline reading-by-reading difference, and average peak difference. Standard deviations were also calculated for each of these measures to quantify their variance.

Initial analysis revealed that in some trials, no discernible peak difference was apparent. To rigorously define which trials should be excluded based on an absent peak, a criterion was devised to exclude any trial in which the peak difference value (defined above) was less than one standard deviation from the baseline difference average. In these cases, no alignment was carried out and the baseline epoch was defined as time points up to and including 5,200 ms. In cases where none of the five trials yielded discernible peaks, no peak value is reported. Additionally, the initial (i.e., 130 ms) reading would occasionally diverge conspicuously from the other baseline values, and would also sometimes appear as two different values within approximately 5 ms. In the latter case, the first value was disregarded. To avoid skewing of the baseline by inaccurate initial readings, any initial values more than two and a half standard deviations from the baseline average were also excluded.

In order to compare the sensitivity of each muscle and finger combination relative to the background level of variation, the signal-to-noise ratio (SNR) was calculated for each. This was accomplished by taking the average peak difference value (i.e. the "signal" of interest) and dividing it by the standard deviation of the corresponding baseline difference value (i.e., the "noise"). The SNR value gives an indication of how easy it will be for a classifier algorithm to detect a deliberately triggered muscle onset while ignoring random fluctuations in the signal. A larger SNR means unintentional noise is less likely to be classified as an onset (i.e., a false positive) and the detection threshold can be set to a higher value relative to the baseline; the higher this threshold, the less likely the signal is to be missed as an onset (i.e., a false negative).

Of the 75 trials (25 per muscle×3 muscles), all successfully yielded EMG recordings. The flexor carpi ulnaris EMG summary statistics are listed in Table 1. Peaks corresponding to the motor task were evident for all five fingers, as seen in the plots of EMG signal values for each trial (FIG. 4A) and calculated reading-by-reading differences (FIG. 4B). The brachioradialis EMG summary statistics are listed in Table 2. Peaks in the EMG signal were not distinguishable for any fingers except for the thumb, as seen in the plots of EMG signal values for each trial (FIG. 5A) and calculated reading-by-reading differences (FIG. 5B). The flexor carpi radialis summary statistics are listed in Table 3. Peaks corresponding to the motor task were evident for four fingers, as seen in the plots of EMG signal values for each trial (FIG. 6A) and calculated reading-by-reading differences (FIG. 6B).

TABLE 1

Electromyography summary statistics for the flexor carpi ulnaris

| Finger | Baseline (mV) | Peak (mV) | Baseline Difference (mV) | Peak Difference (mV) | SNR |
|---|---|---|---|---|---|
| Thumb | 30.4 ± 5.4 | 54.6 ± 6.5 | 0.3 ± 5.3 | 24.2 ± 6.4 | 4.6 |
| Index | 40.4 ± 5.0 | 61 ± 6.0 | 0.7 ± 4.4 | 13.6 ± 2.6 | 3.1 |
| Middle | 39.4 ± 9.7 | 54.8 ± 15.4 | −0.8 ± 7.3 | 19.4 ± 10.4 | 2.7 |
| Ring | 41.1 ± 7.0 | 61.6 ± 7.1 | −0.8 ± 5.1 | 20 ± 5.3 | 3.9 |
| Little | 36.8 ± 8.0 | 51.8 ± 11.9 | −0.5 ± 6.9 | 16.2 ± 8.8 | 2.3 |

(average across five trials ± standard deviation)

TABLE 2

Electromyography summary statistics for the brachioradialis

| Finger | Baseline (mV) | Peak (mV) | Baseline Difference (mV) | Peak Difference (mV) | SNR |
|---|---|---|---|---|---|
| Thumb | 21.1 ± 4.3 | 35.4 ± 2.3 | 0.4 ± 3.1 | 11.6 ± 4.3 | 3.7 |
| Index | 20.5 ± 3.9 | N/A | 0.1 ± 2.9 | N/A | N/A |
| Middle | 22.1 ± 5.1 | N/A | −0.5 ± 3.3 | N/A | N/A |
| Ring | 24.6 ± 4.2 | N/A | 0.1 ± 3.2 | N/A | N/A |
| Little | 21.4 ± 3.8 | N/A | 0.3 ± 2.9 | N/A | N/A |

(average across five trials ± standard deviation)

TABLE 3

Electromyography summary statistics for the flexor carpi radialis

| Finger | Baseline (mV) | Peak (mV) | Baseline Difference (mV) | Peak Difference (mV) | SNR |
|---|---|---|---|---|---|
| Thumb | 9.8 ± 1.7 | 14.2 ± 1.3 | 0.1 ± 1.5 | 3.4 ± 0.5 | 2.3 |
| Index | 10.3 ± 2.0 | 13.2 ± 1.9 | −0.2 ± 1.5 | 4 ± 1.4 | 2.7 |
| Middle | 17.7 ± 3.7 | 24.8 ± 5.2 | 0.1 ± 4.3 | 6.8 ± 1.8 | 1.6 |
| Ring | 14.6 ± 6.3 | 25.8 ± 7.0 | 0.5 ± 3.4 | 10 ± 10.2 | 2.9 |
| Little | 12.4 ± 5.1 | N/A | 0.2 ± 2.9 | N/A | N/A |

(average across five trials ± standard deviation)

Discussion/Conclusions: As indicated in the Results, clear EMG readings were obtained using the setup described in the Methods. Consistent with the hypotheses, the deliberate muscle activity at the onset of the motor task showed a clearly distinct pattern for the flexor carpi ulnaris and the flexor carpi radialis, indicated by the peaks seen in FIGS. 4A, 4B, 6A, and 6B. By contrast, the motor task onset was not consistently evident for the brachioradialis. Interestingly, however, the deliberate muscle activity at the offset of the task can be observed for the brachioradialis after 10,000 ms (FIGS. 5A and 5B). Motor activity during task offset was not clearly apparent for the flexor carpi ulnaris and was only partially apparent for the flexor carpi radialis. Also as hypothesized, an optimal target muscle was determined. After having retrieved data from the three muscles in various locations along the forearm, the flexor carpi ulnaris was determined to output the most precise and accurate readings in a multitude of trials across fingers, in that the flexor carpi ulnaris electrode showed a clear activity peak associated with the onset of the motor task and minimal activity otherwise. Quantitatively, the flexor carpi ulnaris also consistently yielded the highest SNR values. While the onset of the motor task was also apparent for the flexor carpi radialis, this was less consistent across trials and more activity was seen at other times throughout the task. As noted previously, the brachioradialis did not yield a discernible motor onset peak.

One difficulty in using forearm EMG to control a prosthetic is that all of the muscles that control the fingers are anatomically "deep" (i.e., toward the bone) while the ones that control the wrist are "superficial" (i.e., closer to the surface). Therefore, a simple surface EMG setup will necessarily only interface with muscles that control the wrist. However, this experiment indicates that this is not an insurmountable problem, as consistent surface muscle activity was still seen during the finger-specific motor task. This is likely due to the way fingers and wrists act together during natural hand motions. Additionally, selecting a muscle that contributes to wrist motion in typical writing is preferable, as this will make use of the prosthetic feel more natural. The most optimal of the muscles tested was the flexor carpi ulnaris. This muscle has previously been documented to contribute to wrist flexion, or bending inward, which is one type of motion the wrist would normally make when writing. For the flexor carpi ulnaris, the Thumb tests had an average SNR of 4.6, nearly 18% greater than the next highest SNR for that muscle, which was 3.9 for the Ring finger, and nearly 40% greater than the mean SNR of 3.3 across all five fingers for the flexor carpi ulnaris. This responsiveness to thumb activity is also beneficial for naturalistic prosthetic writing, as the thumb normally contributes to both holding and precisely moving writing utensils.

The ultimate objective of this experiment and others to follow is to establish a robust protocol allowing for finger movement upon intentional, biologically controlled activation of a forearm muscle using a combination of EMG recording and a processing algorithm currently in development. This type of setup will mimic the normal biological process of neuronal finger control, in which muscles are activated by electrochemical activity at the neuromuscular junction. During muscle activation, the membrane potential of the axon rapidly increases ("depolarization") then decreases ("repolarization") relative to the resting membrane potential of approximately −65 mV over approximately 10 ms. This fluctuation triggers the release of neurotransmitters at the neuromuscular junction that trigger the muscle to contract. The proposed design will follow a similar scheme in which, upon the EMG signal hitting a threshold, a signal will be sent to motors in a prosthetic hand to initiate finger motions for writing. Future work will emphasize 1) development of a reliable control algorithm, 2) testing additional subjects, and 3) developing additional motor tasks to more accurately reflect natural writing conditions.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the invention disclosed herein. All references cited herein are incorporated by reference in their entirety and made part of this application.

What is claimed is:

1. A prosthetic hand for a subject, comprising:
   a hand body;
   at least two fingers;
   a controller that utilizes a neuronal signal from the subject during a controlled motor activity to determine a threshold, wherein the controller is configured to initiate a motion of at least one finger while gripping and when the threshold has been exceeded, wherein the motion is different than a movement associated with the gripping to create a stroke, the controller causing the motion by moving the at least one finger between an inactivated position to an activated position when the threshold has been exceeded, and wherein a finger of the at least two fingers is bent in the inactivated position.

2. The prosthetic hand of claim 1, wherein the at least two fingers are positioned to accept a tool when the neuronal signal is below the threshold in the inactivated position.

3. The prosthetic hand of claim 1, wherein the finger comprises a joint, the finger being bent at the joint in the inactivated position.

4. The prosthetic hand of claim 1, wherein the controller is configured to detect electrical signals from a flexor carpi ulnaris muscle of the subject, and wherein the electrical signals is based on the neuronal signal.

5. The prosthetic hand of claim 1, wherein the threshold is calculated based on a combination of neuronal signals, and wherein the threshold is a ratio of a peak neuronal signal of a muscle during the controlled motor activity to a baseline signal of the muscle without any motor activity.

6. The prosthetic hand of claim 5, wherein the peak neuronal signal is an average peak signal and the baseline signal is a standard deviation of a previously detected baseline neuronal signal.

7. The prosthetic hand of claim 1, further comprising a tool held by the at least one finger, wherein the motion is a stroke of the tool in response to the neuronal signal having an elevated level that exceeds the threshold.

8. The prosthetic hand of claim 1, wherein the motion comprises painting or brushing teeth using a tool held by the at least one finger including a painting utensil or a toothbrush, respectively.

9. The prosthetic hand of claim 1, wherein the motion, in response to the neuronal signal having an elevated level that exceeds the threshold, comprises a writing motion.

10. The prosthetic hand of claim 1, wherein the prosthetic hand is configured to initiate the motion using a writing utensil.

11. The prosthetic hand of claim 1, further comprising an electrode configured to be placed on a surface of skin of the subject, wherein the neuronal signal is determined from the electrode.

12. The prosthetic hand of claim 11, wherein the electrode is configured to be placed on a forearm.

13. The prosthetic hand of claim 1, wherein the neuronal signal is determined from an implantable device.

14. The prosthetic hand of claim 1, wherein the controller is configured to return the at least one finger to the inactivated position after the motion is completed.

15. The prosthetic hand of claim 1, wherein the controller is configured to:
   determine a baseline neuronal signal of a muscle without any motor activity;
   determine an elevated neuronal signal of the muscle during the controlled motor activity;
   compute the threshold based on a combination of the elevated neuronal signal and the baseline neuronal signal;
   discriminate between intentional and unintentional muscle contractions based on the threshold; and
   facilitate activation of the prosthetic hand when the threshold has been exceeded to effect the motion of the at least one finger during the gripping.

16. The prosthetic hand of claim 15, wherein the threshold is a ratio of a peak neuronal signal of a muscle during the controlled motor activity to a baseline signal of the muscle without any motor activity.

17. The prosthetic hand of claim 16, wherein the peak neuronal signal is an average peak signal and the baseline signal is a standard deviation of a previously detected baseline neuronal signal.

\* \* \* \* \*